(12) United States Patent
Lind et al.

(10) Patent No.: US 9,283,115 B2
(45) Date of Patent: Mar. 15, 2016

(54) PASSIVE TO ACTIVE STAGED DRAINAGE DEVICE

(71) Applicant: ALCON RESEARCH, LTD., Fort Worth, TX (US)

(72) Inventors: Casey Jean Lind, Orange, CA (US); Cesario Pereira Dos Santos, Aliso Viejo, CA (US)

(73) Assignee: Novartis AG, Basel (CH)

( * ) Notice: Subject to any disclaimer, the term of this patent is extended or adjusted under 35 U.S.C. 154(b) by 263 days.

(21) Appl. No.: 13/975,729

(22) Filed: Aug. 26, 2013

(65) Prior Publication Data

US 2015/0057596 A1    Feb. 26, 2015

(51) Int. Cl.
*A61M 5/00* (2006.01)
*A61F 9/007* (2006.01)
*A61B 3/16* (2006.01)

(52) U.S. Cl.
CPC ............... *A61F 9/00781* (2013.01); *A61B 3/16* (2013.01); *A61F 2250/0002* (2013.01)

(58) Field of Classification Search
CPC . A61F 9/00781; A61F 9/00761; A61F 9/007; A61F 9/0017; A61B 5/0084; A61M 27/002
USPC ........... 604/8, 9; 606/107, 108; 623/4.1, 1.12; 424/422, 423
See application file for complete search history.

(56) References Cited

U.S. PATENT DOCUMENTS

| | | | |
|---|---|---|---|
| 4,089,329 A | 5/1978 | Couvillon, Jr. et al. |
| 4,206,762 A | 6/1980 | Cosman |
| 4,457,757 A | 7/1984 | Molteno |
| 4,560,375 A | 12/1985 | Schulte et al. |
| 4,656,827 A | 4/1987 | Puillet |
| 4,750,901 A | 6/1988 | Molteno |
| 4,869,282 A | 9/1989 | Sittler et al. |
| 4,922,913 A | 5/1990 | Waters, Jr. et al. |

(Continued)

FOREIGN PATENT DOCUMENTS

| | | |
|---|---|---|
| CN | 101360523 A | 2/2009 |
| CN | 101466299 A | 6/2009 |

(Continued)

OTHER PUBLICATIONS

Yasukawa T et al., 2001, "Biodegradable scleral plugs for vitreoretinal drug delivery", Adv. Drug Del Rev., 52(1), 25-36.

(Continued)

*Primary Examiner* — Philip R Wiest
(74) *Attorney, Agent, or Firm* — Kenneth D. Bassinger

(57) ABSTRACT

Described herein is an IOP control system for implantation in an eye of a patient, comprising a drainage device and a control device. The drainage system includes a housing including an inlet port and an outlet port, a fluid flow passageway extending from the inlet port to the outlet port to allow the flow of fluid therethrough, and at least one valve disposed within the housing. The at least one valve includes a first side and an opposing second side, and is configured to affect flow through the fluid flow passageway from the inlet port to the outlet port by moving in response to pressure differentials acting on the opposing sides. The control device comprises an actuator including an activated mode and a deactivated mode, and the actuator in the activated mode is configured to selectively adjust flow through the drainage device in response to changes in intraocular pressure.

6 Claims, 8 Drawing Sheets

(56) References Cited

U.S. PATENT DOCUMENTS

| | | |
|---|---|---|
| 5,005,577 A | 4/1991 | Frenkel |
| 5,083,742 A | 1/1992 | Wylie et al. |
| 5,178,604 A | 1/1993 | Baerveldt et al. |
| 5,179,953 A | 1/1993 | Kursar |
| 5,397,300 A | 3/1995 | Baerveldt et al. |
| 5,433,701 A | 7/1995 | Rubinstein |
| 5,466,233 A | 11/1995 | Weiner et al. |
| 5,476,445 A | 12/1995 | Baerveldt et al. |
| 5,558,629 A | 9/1996 | Baerveldt et al. |
| 5,573,646 A | 11/1996 | Saito et al. |
| 5,626,558 A | 5/1997 | Suson |
| 5,681,275 A | 10/1997 | Ahmed |
| 5,707,643 A | 1/1998 | Ogura et al. |
| 5,910,110 A | 6/1999 | Bastable |
| 6,007,511 A | 12/1999 | Prywes |
| 6,048,328 A | 4/2000 | Haller et al. |
| 6,251,090 B1 | 6/2001 | Avery et al. |
| 6,447,449 B1 | 9/2002 | Fleischman et al. |
| 6,468,283 B1 | 10/2002 | Richter et al. |
| 6,579,235 B1 | 6/2003 | Abita et al. |
| 6,589,198 B1 | 7/2003 | Soltanpour et al. |
| 6,682,500 B2 | 1/2004 | Soltanpour et al. |
| 6,712,764 B2 | 3/2004 | Jeffries et al. |
| 6,719,750 B2 | 4/2004 | Varner et al. |
| 6,749,568 B2 | 6/2004 | Fleischman et al. |
| 6,939,299 B1 | 9/2005 | Petersen et al. |
| 6,976,982 B2 | 12/2005 | Santini, Jr. et al. |
| 7,137,952 B2 | 11/2006 | Leonardi et al. |
| 7,169,106 B2 | 1/2007 | Fleischman et al. |
| 7,252,006 B2 | 8/2007 | Tai et al. |
| 7,354,416 B2 | 4/2008 | Quiroz-Mercado et al. |
| 7,409,863 B2 | 8/2008 | Bateman et al. |
| 7,544,176 B2 | 6/2009 | Rodgers et al. |
| 7,612,328 B2 | 11/2009 | Kaiser |
| 7,756,559 B2 | 7/2010 | Abreu |
| 7,824,699 B2 | 11/2010 | Ralph et al. |
| 8,182,435 B2 | 5/2012 | Dacquay et al. |
| 8,206,440 B2 * | 6/2012 | Guarnieri ............ A61F 9/00781 604/8 |
| 8,257,295 B2 | 9/2012 | Rickard et al. |
| 8,419,673 B2 | 4/2013 | Rickard |
| 2001/0000527 A1 | 4/2001 | Yaron et al. |
| 2002/0019607 A1 | 2/2002 | Bui |
| 2002/0049374 A1 | 4/2002 | Abreu |
| 2002/0087111 A1 | 7/2002 | Ethier et al. |
| 2002/0099359 A1 | 7/2002 | Santini, Jr. et al. |
| 2002/0139947 A1 | 10/2002 | Wang |
| 2002/0143284 A1 | 10/2002 | Tu et al. |
| 2002/0193674 A1 | 12/2002 | Fleischman et al. |
| 2003/0014036 A1 | 1/2003 | Varner et al. |
| 2003/0078487 A1 | 4/2003 | Jeffries et al. |
| 2003/0225318 A1 | 12/2003 | Montegrande et al. |
| 2004/0013702 A1 | 1/2004 | Glover |
| 2004/0059248 A1 | 3/2004 | Messner et al. |
| 2004/0073137 A1 | 4/2004 | Lloyd et al. |
| 2004/0111050 A1 | 6/2004 | Smedley et al. |
| 2004/0116794 A1 | 6/2004 | Fink et al. |
| 2004/0186367 A1 | 9/2004 | Fresco |
| 2004/0254438 A1 | 12/2004 | Chuck et al. |
| 2004/0254517 A1 | 12/2004 | Quiroz-Mercado et al. |
| 2005/0159660 A1 | 7/2005 | Montegrande et al. |
| 2005/0271704 A1 | 12/2005 | Tu et al. |
| 2005/0273033 A1 | 12/2005 | Grahn et al. |
| 2006/0131350 A1 | 6/2006 | Schechter et al. |
| 2007/0019156 A1 | 1/2007 | Fink |
| 2007/0032757 A1 | 2/2007 | Medow et al. |
| 2007/0077270 A1 | 4/2007 | Wen |
| 2007/0109117 A1 | 5/2007 | Heitzmann et al. |
| 2007/0123767 A1 | 5/2007 | Montegrande et al. |
| 2007/0129623 A1 | 6/2007 | Fleischman et al. |
| 2007/0212397 A1 | 9/2007 | Roth |
| 2008/0015421 A1 | 1/2008 | Penner |
| 2008/0027478 A1 | 1/2008 | Connors |
| 2008/0077127 A1 | 3/2008 | Gao et al. |
| 2008/0097276 A1 | 4/2008 | Bertrand et al. |
| 2008/0125691 A1 | 5/2008 | Yaron et al. |
| 2008/0129486 A1 | 6/2008 | Jeckelmann et al. |
| 2008/0147021 A1 | 6/2008 | Jani |
| 2008/0228127 A1 | 9/2008 | Burns et al. |
| 2009/0069648 A1 | 3/2009 | Irazoqui et al. |
| 2009/0076367 A1 | 3/2009 | Sit et al. |
| 2009/0143713 A1 | 6/2009 | Van Dam et al. |
| 2009/0227933 A1 | 9/2009 | Karageozian |
| 2009/0240215 A1 | 9/2009 | Humayun et al. |
| 2009/0275924 A1 | 11/2009 | Lattanzio et al. |
| 2009/0312742 A1 | 12/2009 | Pang et al. |
| 2010/0010416 A1 | 1/2010 | Juan, Jr. et al. |
| 2010/0042209 A1 | 2/2010 | Guarnieri |
| 2010/0121248 A1 | 5/2010 | Yu et al. |
| 2010/0174272 A1 | 7/2010 | Weiner |
| 2010/0222769 A1 | 9/2010 | Meng et al. |
| 2010/0234717 A1 | 9/2010 | Wismer |
| 2010/0253167 A1 | 10/2010 | Charnley et al. |
| 2010/0305550 A1 | 12/2010 | Meng et al. |
| 2011/0046536 A1 | 2/2011 | Stegmann et al. |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0248671 A1 | 10/2011 | Dos Santos et al. |

FOREIGN PATENT DOCUMENTS

| | | |
|---|---|---|
| DE | 1438201 | 5/1996 |
| EP | 2427097 | 3/2012 |
| WO | 9303665 | 3/1993 |
| WO | 9803665 | 1/1998 |
| WO | 9803809 | 1/1998 |
| WO | 9938470 A2 | 8/1999 |
| WO | 9938470 A3 | 10/1999 |
| WO | 0194784 | 12/2001 |
| WO | 02056758 | 7/2002 |
| WO | 03001991 | 1/2003 |
| WO | 03102632 | 12/2003 |
| WO | 2005088417 | 9/2005 |
| WO | 2007127305 A2 | 11/2007 |
| WO | 2007136993 | 11/2007 |
| WO | 2008061043 A2 | 5/2008 |
| WO | 2008084350 | 7/2008 |
| WO | 2008061043 A3 | 9/2008 |
| WO | 2009010799 | 1/2009 |
| WO | 2009026499 | 2/2009 |
| WO | 2009049686 | 4/2009 |
| WO | 2009081031 | 7/2009 |
| WO | 2009081031 A3 | 9/2009 |
| WO | 2010129446 A1 | 11/2010 |
| WO | 2010136071 A1 | 12/2010 |
| WO | 2011034727 A1 | 3/2011 |
| WO | 2011034738 A1 | 3/2011 |
| WO | 2011034740 A1 | 3/2011 |
| WO | 2011034742 A2 | 3/2011 |
| WO | 2011035218 A1 | 3/2011 |
| WO | 2011034742 A3 | 5/2011 |
| WO | 2012012017 | 1/2012 |
| WO | 2013052332 A1 | 4/2013 |
| WO | 2013058943 A1 | 4/2013 |

OTHER PUBLICATIONS

Barton, Keith, et al., "The Ahmed Baerveldt Comparison Study," Journal of Ophthalmology, Jul. 15, 2010, vol. 118, No. 3, Elsevier, Inc., USA.

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 166-469, Lyon, France.

Greene, M.E. and Gilman, B.G., "Intraocular Pressure Measurement With Instrumented Contact Lenses," Investigative Ophthalmology &

(56) References Cited

OTHER PUBLICATIONS

Visual Science (IVOS), Apr. 1974, pp. 299-302, vol. 13, No. 4, IVOS.
Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.
International Searching Authority, International Preliminary Report on Patentability, PCT/US2012/057261, May 1, 2014, 9 pages.
International Searching Authority, International Search Report of the International Searching Authority, PCT/US2010/047612, Dec. 21, 2010, 7 pages.
International Searching Authority, International Search Report, PCT/US2012/067747, Apr. 2, 2013, 4 pages.
International Searching Authority, International Search Report, PCT/US2012/068878, Mar. 3, 2013, 5 pages.
International Searching Authority, International Search Report, PCT/US2013/026066, Apr. 17, 2013, 5 pages.
International Searching Authority, Invitation to Pay Additional Fees and, Where Applicable, Protest Fee (Partial Search Report attached), PCT/US2012/067741, Apr. 2, 2013, 6 pages.
International Searching Authority, Search Report and Written Opinion of the International Searching Authority, PCT/US2010/033329, Jul. 13, 2010, 15 pages.
International Searching Authority, Search Report and Written Opinion of the International Searching Authority, PCT/US2010/047429, Nov. 1, 2010, 15 pages.
International Searching Authority, Search Report and Written Opinion of the International Searching Authority, PCT/US2010/047600, Dec. 14, 2010, 13 pages.
International Searching Authority, Search Report and Written Opinion of the International Searching Authority, PCT/US2010/049424, Nov. 26, 2010, 15 pages.
International Searching Authority, Search Report of the International Searching Authority, PCT/US2011/036742, Aug. 17, 2011, 2 pages.
International Searching Authority, Search Report of the International Searching Authority, PCT/US2012/057261, Jan. 23, 2013, 7 pages.
International Searching Authority, Written Opinion of the International Searching Authority, PCT/US2010/047605, Dec. 16, 2010, 9 pages.
International Searching Authority, Written Opinion of the International Searching Authority, PCT/US2010/047612, Dec. 21, 2010, 10 pages.
International Searching Authority, Written Opinion of the International Searching Authority, PCT/US2012/057261, Jan. 23, 2013, 10 pages.
International Searching Authority, Written Opinion of the International Searching Authority, PCT/US2012/068878, Mar. 3, 2013, 8 pages.
International Searching Authority, Written Opinion of the International Searching Authority, PCT/US2013/026066, Apr. 17, 2013, 8 pages.
International Searching Authority, Written Opinion of the International Searching Authority, PCT/US2012/067747, Apr. 2, 2013, 7 pages.
Kuppermann B D et al., 2006, "Efficacy and safety of a novel intravitreous dexamethasone drug-delivery system after applicator or incisional placement in patients with macular edema", IOVS, 47 ARVO E-Abs 5913.
Lam, Andrew K.C. and Douthwaite, William A., "The Effect of an Artificially Intraocular Pressure on the Central Corneal Curvature," Ophlthamic and Physiological Optics, 1997, pp. 18-24, vol. 17, No. 1, Elsevier Science, Ltd., Great Britain.
Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.
Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.

McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Miyamoto H et al., 1997, Biodegradable scleral implant for intravitreal controlled release of fluconazole, Curr Eye Res, 16(9), 930-935.
Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.
Mruthyunjaya P et al., 2003, "An intravitreal sustained release fluocinolone acetonide device to treat severe experimental uveitis", IOVS, 44, ARVO E-Abs 4215.
Neagu Cristina R.; "A Medical Microactuator Based on an Electrochemical Principle"; Thesis at the Twente University,the Netherlands, Enschede; Aug. 28, 1998; pp. 1-162.
Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.
Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.
Ratanapakorn T et al., 2005, "Helical intravitreal triamcinolone implant: An explanation survival study", IVOS 46 E-Abs 484.
Rego MGR et al., 2004, "In vitro evaluation of sustained-release intravitreal dexamethasone implants", IOVS, 45 E-Abs 5060.
Sakurai E et al., 2001, "Scleral plug of biodegradable polymers containing ganciclovir for experimental cytomegalovirus retinitis", IOVS, 42(9), 2043-2048.
Saloomeh Saati MD., Ronalee Lo PhD, Po-Ying Li PhD, Ellis Meng PhD, Rohit Varma MD MPH, and Mark S. Humayun MD PhD; "Mini Drug Pump for Ophthalmic Use"; TRANS Am Ophthalmol Soc 2009; 107; pp. 60-71.
Schnakenberg, U., et al, "Initial Investigations on Systems for Measuring Intraocular Pressure," Sensors and Actuators, 2000, p. 287-291, vol. 85, Elsevier Science B.V., Germany.
See R F et al., 2006, "Safety and drug release profile of injectable intravitreal sustained-release fluocinolone acetonide device", IOVS, 47, ARVO E-Abs 5119.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Stemme, E. and Stemme, G.; "A Valveless Diffuser/Nozzle-Based Fluid Pump"; ScienceDirect; Sensors and Actuators A, 39 (1993); pp. 159-167.
Tano R et al., 2005, Helical intravitreal implant: surgical method development and outcomes, IOVS, 46, ARVO E-Abs 483.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.
Varner S E et al., 2003, "Development of a minimally invasive intravitreal implant for drug delivery", IOVS, 44, ARVO E-Abs 4214.
"Walter, Peter; Intraocular Pressure Sensor: Where Are We—Where Will We Go? Journal Graefe's Archive for clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject collection Medicine."
Weiner A L, 2007, "Drug Delivery Systems in Ophthalmic Applications, In: Ocular Therapeutics; Eye on New Discoveries; T. Yorio, A. Clark, M.Wax, Eds, Elsevier Press/Academic Press, New York", pp. 7-43.

* cited by examiner

PASSIVE TO ACTIVE STAGED DRAINAGE DEVICE

BACKGROUND

The present disclosure relates generally to valves and associated systems and methods. In some instances, embodiments of the present disclosure are configured to be part of an intraocular pressure (IOP) control system for use in ophthalmic treatments.

Glaucoma, a group of eye diseases affecting the retina and optic nerve, is one of the leading causes of blindness worldwide. Most forms of glaucoma result when the IOP increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

FIG. 1 is a diagram of the front portion of an eye that helps to explain the processes of glaucoma. In FIG. 1, representations of the lens 10, cornea 20, iris 30, ciliary body 40, trabecular meshwork 50, and Schlemm's canal 60 are pictured. Anatomically, the anterior segment of the eye includes the structures that cause elevated IOP which may lead to glaucoma. Aqueous humor fluid is produced by the ciliary body 40 that lies beneath the iris 30 and adjacent to the lens 10 in the anterior segment of the eye. This aqueous humor washes over the lens 10 and iris 30 and flows to the drainage system located in the angle of the anterior chamber 70. The angle of the anterior chamber 70, which extends circumferentially around the eye, contains structures that allow the aqueous humor to drain. The trabecular meshwork 50 is commonly implicated in glaucoma. The trabecular meshwork 50 extends circumferentially around the anterior chamber. The trabecular meshwork 50 may act as a filter, limiting the outflow of aqueous humor and providing a back pressure that directly relates to IOP. Schlemm's canal 60 is located beyond the trabecular meshwork 50. Schlemm's canal 60 is fluidically coupled to collector channels (not shown) allowing aqueous humor to flow out of the anterior chamber. The two arrows in the anterior segment of FIG. 1 show the flow of aqueous humor from the ciliary bodies 40, over the lens 10, over the iris 30, through the trabecular meshwork 50, and into Schlemm's canal 60 and its collector channels.

One method of treating glaucoma includes implanting a drainage device in a patient's eye. The drainage device allows fluid to flow from the anterior chamber of the eye to a drainage site, relieving pressure in the eye and thus lowering IOP. These devices are generally passive devices that do not provide a smart, interactive control of the amount of flow through the drainage tube. Once the drainage device is implanted, the body may form a bleb, or fluid-filled space surrounded by scar tissue, at the drainage site into which aqueous humor flows via a drainage tube. Changes at the drainage site such as bleb formation may affect the pressure differentials acting on the drainage device, thereby affecting the passive flow through the device. In order to provide desired treatments to patients, it may be important to actively regulate the flow of aqueous humor through the drainage device into the drainage site.

The system and methods disclosed herein overcome one or more of the deficiencies of the prior art.

SUMMARY

In one exemplary aspect, this disclosure is directed to an IOP control system for implantation in an eye of a patient comprising a drainage device and a control device. In one aspect, the drainage device is sized for implantation in the eye of a patient and includes a housing, a fluid flow passageway, and at least one valve disposed within the drainage device. In one aspect, the housing includes an inlet port and an outlet port, and the fluid flow passageway extends through the housing from the inlet port to the outlet port to allow the flow of fluid from the inlet port to the outlet port. In one aspect, the at least one valve includes a first side and an opposing second side, and is configured to affect flow through the fluid flow passageway from the inlet port to the outlet port by moving in response to pressure differentials acting on the opposing first and second sides. In one aspect, the control device comprises an actuator including an activated mode and a deactivated mode. In one aspect, the actuator in the activated mode is configured to selectively adjust flow through the drainage device in response to changes in intraocular pressure.

In another exemplary embodiment, the present disclosure is directed to a method of regulating drainage from an anterior chamber of an eye. The method comprises directing fluid through an implantable primary drainage device including a housing defining a fluid flow passageway containing at least one valve, the at least one valve configured to respond to an implantable secondary control device to selectively adjust flow through the fluid flow passageway. In one aspect, the method further comprises modifying the amount of drainage through the implantable primary drainage device in response to pressure differentials acting on the at least one valve.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
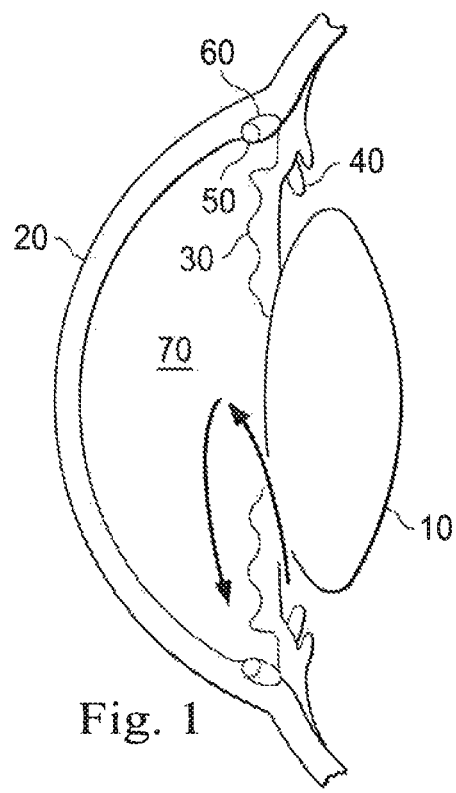
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to a drainage system configured to regulate fluid flow by employing both a passive state and an active state to control the operation of a flow system inside a glaucoma drainage device. In some instances, embodiments of the present disclosure are configured to be used in the operation of drainage devices including a valve flow system. In some instances, embodiments of the present disclosure are configured to be part of an IOP control system comprising a drainage device configured to extend from the anterior chamber of the eye to a drainage site. Those of skill in the art will realize that the systems and devices disclosed herein may be utilized in alternative applications aided by having both a passive state and an active state to control the drainage of fluid through a flow system.

Drainage devices which rely on the pressure differential between the anterior chamber and the drainage site may cause a detrimental hypotonous state by releasing aqueous humor too fast from the anterior chamber after the initial implantation. It is not until a few weeks after implantation that a bleb forms at the drainage site to sufficiently regulate the fluid flow. In addition, progressive scarring of the bleb over time may cause the bleb pressure to increase, resulting in an increase in IOP. Flow systems that rely solely on the pressure differential between the anterior chamber and the drainage site to create flow through the device may eventually fail due to this effect, by increasing the IOP above an acceptable threshold which varies from patient to patient (e.g. 12 mmHg).

The systems and devices disclosed herein allow a user to switch the flow system between a passive, pressure-based mode to an active mode where the user can actively throttle (e.g., open and close) the flow system to regulate flow through the drainage device. In some embodiments, the flow system may switch between the passive mode and the active mode in response to changes in the IOP over time. In one embodiment, the systems and devices disclosed herein pertain to an IOP control system comprising a primary drainage device and an optional secondary control device. In some embodiments, the primary drainage device and the secondary control device are component parts of a single implant.

Figure 2:
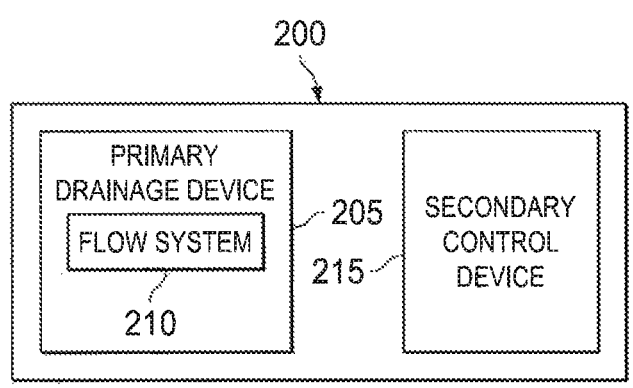
FIG. 2 is a block diagram of an exemplary IOP control system according to the principles of the present disclosure.

FIG. 2 is a schematic block diagram of an exemplary IOP control system 200 usable for the treatment of glaucoma or other ocular conditions according to the principles of the present disclosure. In FIG. 2, the IOP control system 200 comprises a primary drainage device 205 and a secondary control device 215. The primary drainage device 205 is designed to passively open when the pressure differential across a flow system 210 within the drainage device 205 exceeds a threshold value. After a conventional pressure-driven passive drainage device is implanted within the eye, IOP tends to fall rapidly as aqueous fluid flows immediately through the drainage device to a drainage site. In the embodiments disclosed herein, the flow system 210 (described further below) within the drainage device 205 can be actively adjusted (e.g., opened or closed) by the secondary control device 215. Thus, the systems and devices disclosed herein may extend the life of the drainage device 205 by utilizing the secondary control device 215 to actively increase the flow through flow system 210 as the drainage site pressure increases (e.g., as the bleb develops scar tissue).

Figure 3:
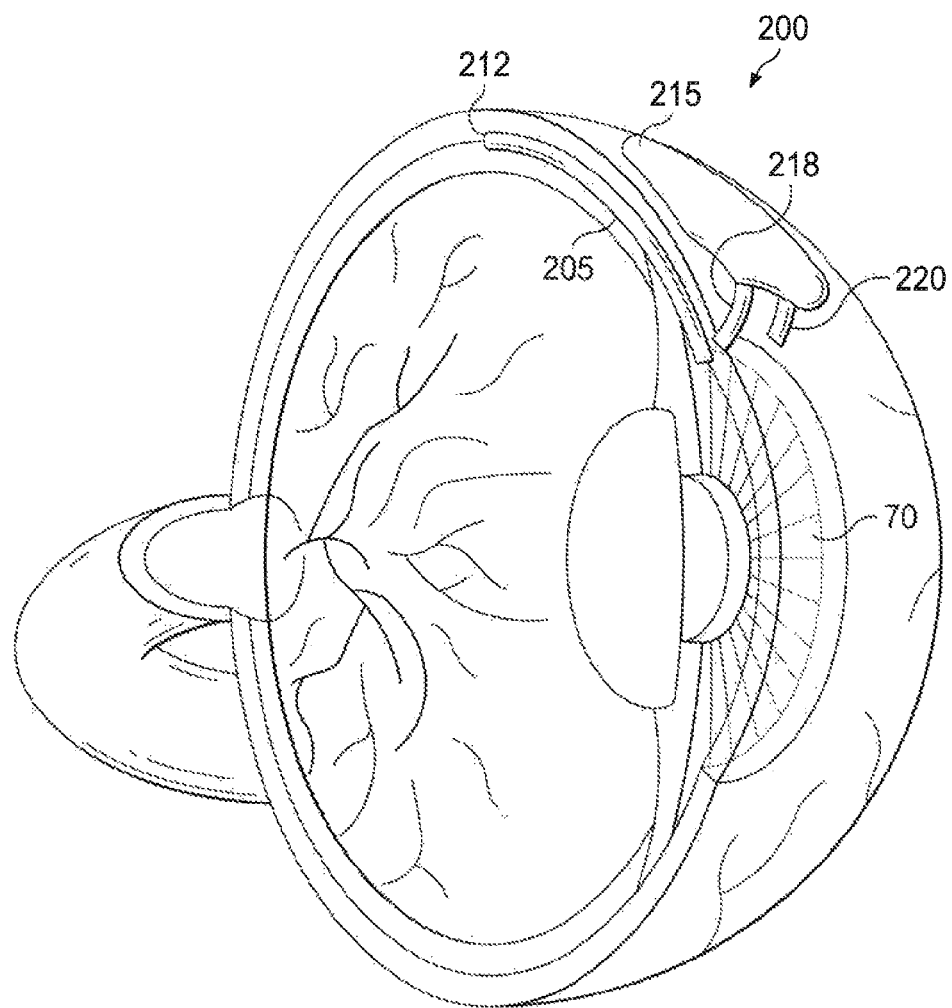
FIG. 3 is an illustration of an exemplary flow-regulating system disposed in the eye in accordance with one embodiment of the present disclosure.

FIG. 3 shows the IOP control system 200 disposed on an eye to treat an ocular condition according to one exemplary aspect of the present disclosure. In the pictured embodiment, the primary drainage device 205 is implanted within the eye to extend from the anterior chamber 70 to a drainage site 212. In the pictured embodiment, the drainage site 212 is the suprachoroidal space. In other embodiments, as described below with reference to FIG. 5, the drainage site 212 may be located elsewhere, such as, by way of non-limiting example, the subconjunctival space. The primary drainage device 205 is configured to carry various components of the IOP control system 200, and may include, by way of non-limiting example, any number of drainage tubes, valves, pumps, transducers, or sensors. In the pictured embodiment, the primary drainage device 205 is configured to fit at least partially within the suprachoroidal space and is sized for example within a range between about 50 µm×50 µm to about 250 µm×250 µm. In some embodiments, the primary drainage device 205 has a thickness less than or equal to about 250 µm. For example, in one embodiment, the primary drainage device 205 has a thickness of about 250 µm. Other sizes and thicknesses are also contemplated. The primary drainage device 205 may be curved to approximate the radius of the eye globe. In some embodiments, the primary drainage device 205 is rigid and preformed with a curvature suitable to substantially conform to the globe. In other embodiments, the primary drainage device 205 is flexible to conform to the globe. The above dimensions and arrangement are exemplary only, and other sizes and arrangements are contemplated.

In the pictured embodiment, the primary drainage device 205 is sized to extend from the anterior chamber 70 of the eye to the drainage site 212 in the suprachoroidal space. The drainage device 205 bridges the anterior chamber 70 and the drainage site 210 to provide an auxiliary flow path for aqueous humor, bypassing the flow-resistive conventional pathway through the trabecular meshwork and shunting aqueous humor directly to the drainage site 212. In the example shown, the primary drainage device 205 is a single hollow tube having a single lumen. Other embodiments include a plurality of tubes or a plurality of lumens cooperating together to permit fluid to flow through the implantable system 200. Aqueous humor may drain through the primary drainage device 205 from the anterior chamber 70 to the drainage site 212 to alleviate elevated intraocular pressure conditions.

In the pictured embodiment, the implantable system 200 includes a secondary control device 215. As described below with reference to FIG. 4, the secondary control device 215 is arranged to carry various components of an IOP control system, and may include transducers or sensors, a processing system, a memory, drug delivery components, a power source, an actuator, and/or other components that may be used to either control the implantable system 200 or otherwise treat ocular conditions. For example, in the pictured embodiment in FIG. 3, an anterior chamber pressure element 218 and an atmospheric pressure reference element 220 form a part of the secondary control device 215 and extend from other parts of the secondary control device 215. In some embodiments, the anterior chamber pressure element 218 comprises a pressure sensor. In some embodiments, the atmospheric pressure reference element 220 comprises a pressure sensor.

When implanted, the secondary control device 215 may be located in the subconjunctival pocket between the conjunctiva and sclera. It may be generally located on an ocular quadrant commonly used for conventional glaucoma drainage devices with plates; that is, it may be located between neighboring ocular muscles that define the ocular quadrant chosen for implantation. In the pictured embodiment, the secondary control device 215 is configured to fit at least partially within the subconjunctival space and is sized for example within a range between about 15 mm×10 mm to about 30 mm×15 mm. In some embodiments, the secondary control device 215 has a thickness less than about 2 mm thick. For example, in one embodiment, the secondary control device 215 has a thickness of about 1 mm thick. The secondary control device 215 may be curved to approximate the radius of the eye globe. In some embodiments, the secondary control device 215 is rigid and preformed with a curvature suitable to substantially conform to the globe. In other embodiments, the secondary control device 215 is flexible to conform to the globe. The above dimensions and arrangement are exemplary only, and other sizes and arrangements are contemplated.

Figure 4:
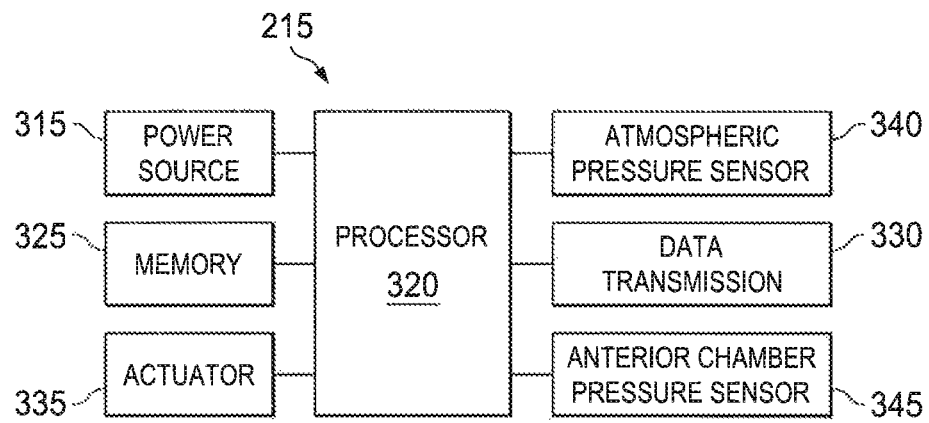
FIG. 4 is a block diagram of an exemplary secondary control device according to the principles of the present disclosure.

FIG. 4 is a block diagram of the exemplary secondary control device 215. The control device 215 can comprise any of a variety of implantable devices, including, by way of non-limiting example, a plate configured for placement on the eye of the patient. In the pictured embodiment, the control device 215 comprises various component parts, including, by way of non-limiting example, a power source 315, a processor 320, a memory 325, a data transmission module 330, an actuator 335, an atmospheric pressure sensor 340, and an anterior chamber pressure sensor 345. The pictured component parts of the secondary control device 215 are for illustrative purposes only, and are not intended to be limiting. In some embodiments, the secondary control device 215 lacks some of these components. For example, in some embodiments, the control device 215 comprises only an actuator 335.

In one embodiment, the actuator 335 is configured to actuate the opening and closing of individual valves within the primary drainage device 205.

The power source 315 is typically a rechargeable battery, such as a lithium ion or lithium polymer battery, although other types of batteries may be employed. In other embodiments, any other type of power cell is appropriate for the power source 315. The power source 315 provides power to the secondary control device 215, and may provide power to the primary drainage device 205. In some examples, sufficient power is provided through on-board batteries and/or wireless powering. The power source 315 can be recharged via inductive coupling such as an RFID link or other type of electromagnetic coupling.

The processor 320 is typically an integrated circuit with power, input, and output pins capable of performing logic functions. For example, the processor 320 may perform logic functions based on inputs from the atmospheric pressure sensor 340 and the anterior chamber pressure sensor 345 to determine the current IOP of the eye and/or the operating status of the IOP control system 200 (note, the IOP is the difference between the anterior chamber pressure and the atmospheric pressure). In some embodiments, the processor 320 controls the supply of power from the power source 315 to the primary drainage device 205 and/or signal commands to the primary drainage device 205. In various embodiments, the processor 320 may be a targeted device controller or a microprocessor configured to control more than one component of the primary drainage device 205 or a combination thereof. The processor 320 may include one or more programmable processor units running programmable code instructions for implementing the pressure threshold modulation methods described herein, among other functions.

The processor 320 may be wirelessly coupled to a computer and/or other types of processor-based devices suitable for a variety of ocular applications. In various embodiments, the processor 320 can receive input data from a user, the atmospheric pressure sensor 340, the anterior chamber pressure sensor 345, the primary drainage device 205, and/or various accessory devices via wireless or wired mechanisms. The processor 320 may use such input data to generate control signals to control or direct the operation of the primary drainage device 205. In some embodiments, the user can program or direct the operation of the primary drainage device 205 through the secondary control device 215. In some embodiments, the processor 320 is in direct wireless communication with the primary drainage device 205, and can receive data from and send commands to the primary drainage device 205.

The memory 325, which is typically a semiconductor memory such as RAM, FRAM, or flash memory, interfaces with the processor 320. As such, the processor 320 can write to and read from the memory 325, and perform other common functions associated with managing semiconductor memory. For example, a series of pressure readings, IOP calculations, and/or command sequences can be stored in the memory 325.

The processor 320 and/or the memory 325 may also include software containing one or more algorithms defining one or more functions or relationships between command signals and input data (received from the primary drainage device 205, and/or accessory devices). The algorithm may dictate activation or deactivation command protocols/signals (e.g., to the actuator 335) depending on the received input data or mathematical derivatives thereof. In some embodiments, the algorithm may dictate activation or deactivation control signals affecting particular valves on the primary drainage device 205 when the input data indicates an IOP below a predetermined threshold value, above a predetermined threshold value, and/or when the input data indicates a specific physiologic event, temporal state, or pathologic condition (e.g., hypotony, bleb scarring, or an initial post-operative state). The processor 320 may be configured to selectively implement one or more control algorithms to enable IOP control. In some embodiments, the processor 320 may be re-programmed to selectively implement one or more particular control algorithms.

In various embodiments, the secondary control device 215 may be operatively coupled to the primary drainage device 205 by way of wired or wireless communication mechanisms. In some embodiments, the external IOP control device 215 may affect the primary drainage device 205 by either (1) utilizing wireless communication between the primary drainage device 205 and the secondary control device 215, or (2) utilizing trans-scleral connections between the secondary control device 215 and the primary drainage device 205. Contemplated wireless communication methods include, by way of non-limiting example, cooperating transmitters and receivers positioned on various components of the IOP control system 200 to allow remote communication between various components of the system 200 (shown in FIG. 2).

Thus, the data transmission module 330 may employ any of a number of different types of data transmission. For example, in various embodiments, the data transmission module 330 may be an active device such as a radio or a passive device with an antenna capable of wireless communication. In some embodiments, the data transmission module 330 may be activated to communicate the open and closed status of individual valves within the primary drainage device 205 to the secondary control device 215 or other electronic device or service such as, by way of non-limiting example, a PDA, cell phone, computer, remote accessible data storage site (e.g. an internet server, email server, text message server). In some embodiments, control signals or program algorithms may be transmitted to the data transmission module 330 from an external device to adjust the treatment settings.

The actuator 335 is configured to influence the flow system 210 within the primary drainage device 205 to assume an open or closed condition. In particular, the actuator 335 is configured to selectively open valves within the flow system 210 to increase flow through the primary drainage device 205. In some embodiments, the actuator 335 can selectively open individual valves of the flow system 210 independently of each other. In some embodiments, the actuator 335 comprises an electromagnet configured to selectively open and close individual valves within the flow system 210 of the primary drainage device 205. In some embodiments, the actuator 335 can act upon the primary drainage device 205 without the use of the processor 320. In other embodiments, the actuator 335 is controlled by the processor 320.

The atmospheric pressure sensor 340 and the anterior chamber pressure sensor 345 may be the same as the atmospheric pressure reference element 220 and the anterior chamber pressure element 218, respectively, shown in FIG. 3. The atmospheric pressure sensor 340 and the anterior chamber pressure sensor 345 are discussed in further detail below with reference to FIG. 5.

Figure 5:
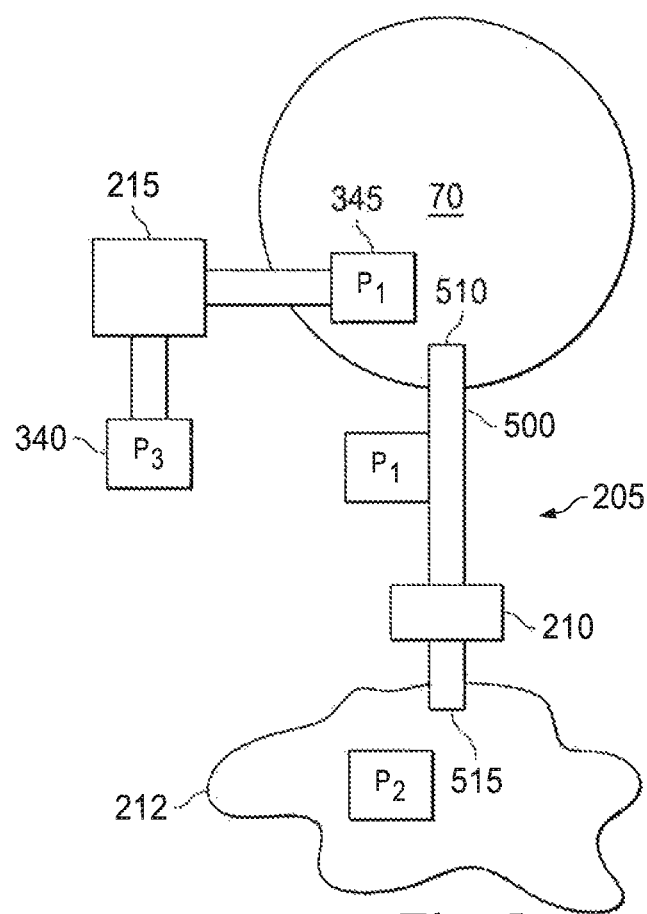
FIG. 5 is a schematic diagram of an exemplary IOP control system disposed within an eye according to the principles of the present disclosure.

FIG. 5 is a schematic diagram of the IOP control system 200 implanted in an eye of a patient for the treatment of glaucoma or other ocular conditions. In the pictured embodiment, both the primary drainage device 205 and the secondary control device 215 are shown implanted into the eye. The primary drainage device 205 is configured in a manner that provides passive IOP pressure control by allowing aqueous humor to drain from the anterior chamber 70 to the drainage site 212. In some embodiments, the secondary control device 215 is implanted in the eye in addition to the primary drainage device 205 to provide active IOP control by affecting the primary drainage device 205 in consideration of the current IOP and/or the patient's treatment stage. In some instances, the utilization of the secondary control device 215 reduces complications arising from surgical implant glaucoma treatments and extends the life of the primary drainage device 205.

In some instances, the primary drainage device 205 and the secondary control device 215 are implanted at different times during different surgical procedures. For example, in some instances, the primary drainage device 205 is initially implanted in the eye, and the secondary control device 215 is later implanted into the eye if a healthcare provider determines that the primary drainage device 205 is not providing adequate IOP control (e.g., as the pressure at the drainage site or bleb increases, resulting in decreased outflow of aqueous humor through the primary drainage device 205). It is important to note, however, that if the primary drainage device 205 provides adequate IOP control, then the secondary control device 215 need not be implanted into the eye.

In some instances, the primary drainage device and the secondary control device are implanted in different anatomic locations. For example, in one instance, the primary drainage device 205 may be implanted between the anterior chamber 70 and the suprachoroidal space, and the secondary control device 215 may be implanted into the subconjunctival space (as illustrated in FIG. 3). In other instances, the primary drainage device and the secondary control device are implanted adjacent to each other within the same anatomic space or location. For example, in one instance, the primary drainage device 205 may be implanted between the anterior chamber 70 and the suprachoroidal space, and the secondary control device 215 may be implanted into the suprachoroidal space.

Figure 6:
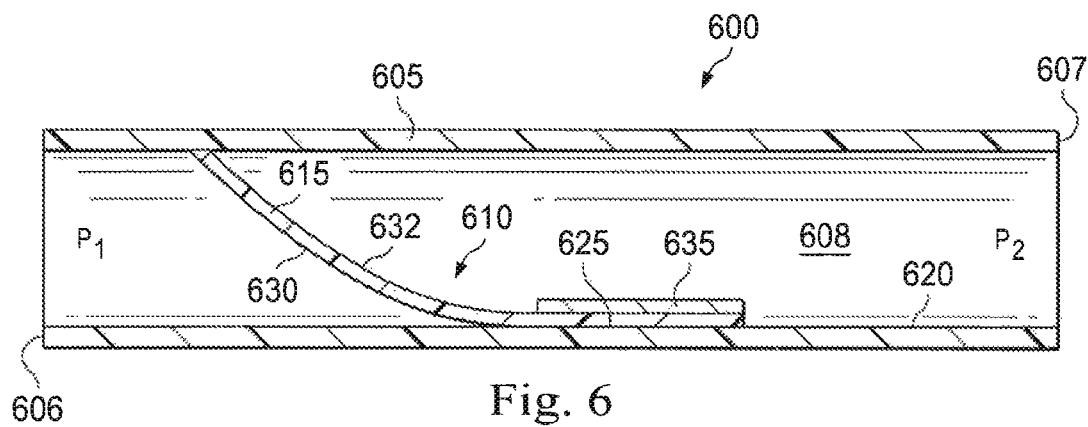
FIG. 6 is a stylized illustration of a cross-sectional view of an exemplary primary drainage device according to the principles of the present disclosure, showing the exemplary flow system in a closed condition.

In the embodiment pictured in FIG. 5, the primary drainage device 205 includes a drainage tube 500 and the flow system 210. The flow system 210 is disposed along, and may form a part of, the drainage tube 500 between a proximal end 510 of the drainage tube in the anterior chamber 70 and a distal end 515 of the drainage tube, which leads to the drainage site 212. The drainage tube 500 drains aqueous humor from the anterior chamber 70 of the eye to the drainage site 212. The flow system 210 controls the flow of aqueous humor through the drainage tube 500 and comprises one or more valves or other passive flow devices for regulating or otherwise affecting flow. For example, in one embodiment, the flow system 210 comprises a series of valves. In the illustrated embodiments herein, the flow system 210 of the primary drainage device 205 comprises a single valve (as shown in FIG. 6).

In FIG. 5, the exemplary primary drainage device 205 includes at least two distinct pressure zones, and may include pressure sensors positioned therein. The pressure zone P1 reflects the pressure of the anterior chamber 70, and the pressure zone P2 reflects the pressure of the drainage site 212. In some embodiments, the pressure zone P1 is located in a lumen or tube that is in fluid communication with the anterior chamber 70, such as the drainage tube 500. In the embodiment shown, the pressure zone P1 reflects the pressure in the tube 500 upstream from the flow system 210 and downstream from the anterior chamber 70. In this manner, pressure zone P1 reflects the pressure in the anterior chamber 70 because the expected measurement discrepancy between the true anterior chamber pressure and pressure within a tube downstream of the anterior chamber (even when located between the sclera and the conjunctiva) is very minimal.

The pressure zone P2 may be located in a pocket at the drainage site 212, such as a bleb, that generally contains aqueous humor. The drainage site 212 may be, by way of non-limiting example, in a subconjunctival space, a suprachoroidal space, a subscleral space, a supraciliary space, Schlemm's canal, a collector channel, an episcleral vein, and a uveo-scleral pathway, among other locations in the eye. The difference between the pressures at zones P1 and P2 (P1–P2) provides an indication of the pressure differential across the flow system 210 (i.e., between the anterior chamber 70 and the drainage site 212). In one embodiment (e.g., where only the primary drainage device 205 in implanted in the eye), this pressure differential dictates the rate of aqueous humor flow from the anterior chamber 70 to the drainage site 212.

In FIG. 5, the exemplary secondary control device 215 includes at least two pressure sensors, the atmospheric pressure sensor 340 and the anterior chamber pressure sensor 345 (as shown in FIG. 3), positioned to measure the pressure within the atmospheric pressure zone P3 and the pressure within the anterior chamber 70, respectively. The anterior chamber pressure sensor 345 is located in or is in fluidic communication with an anterior chamber 70, and the atmospheric pressure sensor 340 is located remotely from zones P1 and P2 in a manner to measure atmospheric pressure.

In some embodiments, the primary drainage device 205 includes pressure sensors (not shown) corresponding to the pressure zones P1 and P2. These primary drainage device sensors and the pressure sensors 340, 345 can be any type of pressure sensors suitable for implantation in the eye. They each may be the same type of pressure sensor, or they may be different types of pressure sensors. In various embodiments, the IOP control system 200 may include any number of pressure sensors or lack pressure sensors altogether.

Generally, IOP is a gauge pressure reading—the difference between the absolute pressure in the eye (e.g., as measured by the anterior chamber pressure sensor 345 in zone P1) and atmospheric pressure (e.g., as measured by the atmospheric pressure sensor 340 in zone P3). In one embodiment of the present disclosure, pressure readings are taken in the pressure zones P1 and P3 simultaneously or nearly simultaneously over time so that the actual IOP can be calculated (as P1–P3 or P1–f(P3), where f(P3) indicates a function of P3). Pressure measurements by any pressure sensors within zones P1, P2, and P3 can be may be stored in a memory source, such as, by way of non-limiting example, the memory 325 by the processor 320. They can later be read from the memory source so that the pressure drop across the primary drainage device 205 over time can be interpreted by a user, such as a patient or a healthcare professional. In some embodiments, the pressure measurements and any calculations derived therefrom (e.g., the IOP) may be visually depicted on a display in any of a variety of forms, including, by way of non-limiting example, graphical and list forms.

The flow system 210 is configured to control the flow of drainage fluid through the drainage tube 500, and thereby affect pressure in the eye, including the IOP. A desired pressure differential can be maintained by controlling the flow through the flow system 210. For example, when the IOP is too high, the flow system 210 may operate to permit increased flow through the drainage tube 500, and when the IOP is too low (e.g., in a hypotonous state where aqueous humor is draining too rapidly from the anterior chamber), the flow system 210 may operate to decrease the flow through the drainage tube 500. Likewise, some embodiments of the IOP control system 200 are configured to control the flow of drainage fluid to the drainage site 212 (e.g., a bleb), and thereby control the bleb pressure to maintain a desired fluid flow to the bleb, decrease fibrosis, and increase absorption efficiency. To accomplish this, the flow system 210 may be responsive to the secondary control device 215 based on input data received from the atmospheric pressure sensor 340, the anterior chamber pressure sensor 345, IOP calculations, and/or a pre-programmed treatment protocol (e.g., based on the current IOP or the time lapse after initial implantation). Such a treatment protocol may be stored in the memory 325 (shown in FIG. 4). In some embodiments, the flow system 210 may be responsive to the actuator 335 of the external IOP control device 215 without the need for processor instructions.

FIG. 6 shows a stylized cross-sectional view of an exemplary flow system 600 in a closed condition. The flow system 600 may be the same as the flow system 210 discussed with reference to FIGS. 2 and 5. The flow system 600 comprises a housing 605 extending from an inlet port or inlet 606 to an outlet port or outlet 607. The housing 605 may connect to the drainage tube 500 or may form a part of the drainage tube 500. The housing 605 includes a fluid flow passageway 608 extending between the inlet 606 and the outlet 607. In the pictured embodiment, the flow system 600 includes a valve 610. In the pictured embodiment, the valve 610 is a flexible cantilever valve. The valve 610 is configured as a flow control valve that can completely or partially block the flow of aqueous humor by deflecting a sealing portion 615 completely or partially across the fluid flow passageway 608. Other embodiments may include any number, type, and arrangement of valves, provided that the valves are capable of selectively restricting the flow of fluid through the fluid flow passageway 608 based on the pressure differential between the pressure zones P1 and P2.

The housing 605 can be shaped in any of a variety of three-dimensional hollow shapes, including, by way of non-limiting example, a curved disc, an oblong plate, and a cylindrical tube. The housing 605 is arranged and configured relative to the drainage tube 500 to allow aqueous humor from the anterior chamber 70 (shown in FIG. 5) to flow into the inlet 606, through the fluid flow passageway 608, past the valve 610, and out the outlet 607 to the drainage site 212 (shown in FIG. 5). In particular, the inlet 606 may be in fluid communication with the drainage tube 500 and is configured to receive aqueous humor flowing from the drainage tube 500 into the fluid flow passageway 608. The outlet 607 permits fluid to exit the fluid flow passageway 608 for release at the drainage site 212. Thus, in the pictured embodiment, the pressure zone P1 is located proximal to the inlet 606 and the pressure zone P2 is located distal to the outlet 607. The fluid flow through the flow system 210 is dependent upon the pressure differential between the pressure zone P1 at the inlet 606 and the pressure zone P2 at the outlet 607 (corresponding to the pressure zones P1 and P2 shown in FIG. 5).

In FIG. 6, the valve 610 is shown in a closed, flow-blocking condition. In the pictured embodiment, the housing 605 is configured to connect with the drainage tube 500 (shown in FIG. 5) such that deflection of the sealing portion 615 at least partially opens and closes the valve 610. The valve 610 and the housing 605 are shaped and configured such that deflection of the sealing portion 615 at least partially opens and closes the valve to the outflow of aqueous humor from the flow system 600. An inner surface 620 of the housing 605 provides a valve seat 625 against which the sealing portion 615 may rest to close the valve 610. The valve seat 625 is shaped and configured such that when the sealing portion 615 rests on the valve seat 625, the valve 610 is in a closed condition.

The sealing portion 615 may be formed of an elastically deformable biocompatible material such as, by way of non-limiting example, silicone, silicon nitride, silicone elastomer, polyimide, Parylene, and others. In the example shown, the sealing portion 615 is shaped as a flexible membrane that is secured at its periphery to the housing 605. The sealing portion 615 comprises a flexible membrane responsive to a pressure differential across a first surface 630 and an opposing second surface 632. In the pictured embodiment, the pressure within the pressure zone P1 acts upon the first surface 630, and the pressure within the pressure zone P2 acts upon the second surface 632. For purposes of practicality, the sealing portion 615 should be thick enough to be durable and resistant to corrosion and leakage. However, the sealing portion 615 should also be thin enough to provide the necessary flexibility and deflection capabilities which are required in a membrane designed for use in a pressure-responsive control system. A preferred thickness of the sealing portion 615 will depend on the deflection response desired for a given pressure and the material chosen. As an example, the sealing portion 615 may be fabricated out of Parylene and may have a thickness ranging from 0.5 μm to 30 μm. In some embodiments, the sealing portion 615 is substantially smooth, without corrugation features. In some embodiments, the sealing portion 615 includes indentations or corrugations whose depths affect the deflection profile of the sealing portion 615 in response to various pressures. The thickness, material, and diameter of the sealing portion 615 as well as the depth, number, and orientation of the corrugations, may affect the cracking pressure and deflection profiles of the sealing portion 615.

In the pictured embodiment, the sealing portion 615 includes a responsive element 635 coupled to the second surface 632 of the sealing portion 615. The responsive element 635 is configured to be responsive to the secondary control device 615. In some embodiments, the responsive element 635 is configured to be responsive to the actuator 335 of the secondary control device 615. In the pictured embodiment, the responsive element 635 comprises a metallic element, deposit, or strip. The responsive element 635 may be formed of any of a variety of metallic materials that are responsive to a magnetic field.

The cracking pressure of a valve generally refers to the minimum pressure differential needed between the entrance and exit of the valve to lift the sealing portion off its valve seat, thereby allowing the valve to assume an open condition allowing fluid flow past the valve. The cracking pressure of the valve 610 is dependent upon the structure and configuration of the sealing portion 615 and structure and configuration of the valve seat 625.

The cracking pressure of the valve 610 is dependent upon the structural characteristics of the sealing portion 615 and the valve seat 625. Therefore, the cracking pressure of the valve 610 is dependent upon the geometry (e.g., shape, diameter, and thickness), and material properties (e.g., stiffness) of the sealing portion 615 as well as the geometry (e.g., size and shape), and material properties (e.g., stiffness) of the valve seat 625. For example, the specific configuration and structure of the valve 610 (e.g., the height of the valve seat 625 within the fluid flow passageway 608 and the diameter of the sealing portion 615, by way of non-limiting example) can be selected to create a particular cracking pressure for the valve. Accordingly, the cracking pressure of the valve 610 may be preselected by controlling these parameters during the manufacturing or assembly processes. In addition, the healthcare provider may select flow system including a valve having a particular cracking pressure based on the most appropriate or desired IOP range for the treatment of a particular condition.

In the described embodiment, the sealing portion 615 is shaped and configured to contact the valve seat 625 when the pressure differential across the valve 610 closes the valve 610, as shown in FIG. 6. If the pressure differential P1:P2 across the sealing portion 615 is less than the cracking pressure of the valve 610, then the sealing portion 615 will remain in contact with the contact surface 562 of the valve seat 560, and the valve 610 will remain in or assume a closed condition. When the valve 610 is in a closed condition, aqueous fluid cannot flow through the valve 610. In particular, the valve 610 will not open to allow aqueous humor to drain through the flow system 600 into the drainage site 212 unless the pressure differential across the valve 610 (P1:P2) overcomes the cracking pressure of the valve 610.

Figure 7:
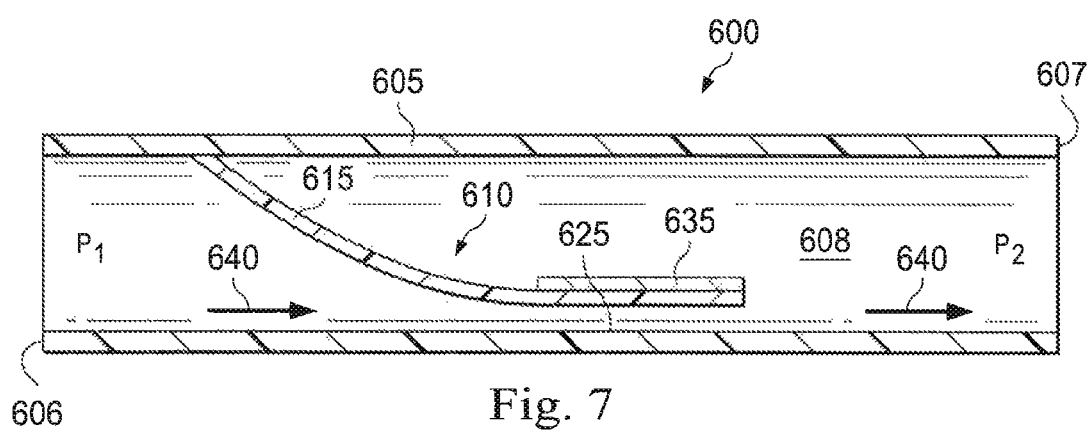
FIG. 7 is a stylized illustration of a cross-sectional view of the exemplary primary drainage device shown in FIG. 6, showing the flow system in an open condition.

FIG. 7 shows a stylized cross-sectional view of the exemplary flow system 600 in an open condition. If the pressure differential P1:P2 across the sealing portion 615 is greater than the cracking pressure of the valve 610, then the sealing portion 615 will deflect away from the valve seat 625 into the fluid flow passageway 608, and the valve 610 will assume an open condition. When the valve 610 is in an open condition, aqueous fluid flows through the valve 610 from the inlet 606 to the outlet 607 in the direction indicated by the arrows 640. The distance of deflection of the sealing portion 615 away from the valve seat 625 depends at least partially upon the degree by which the pressure differential P1:P2 across the sealing portion 615 is greater than the cracking pressure of the valve 610. Thus, the valve 610 may assume varying degrees of an open state or open condition, directly affecting the flow through the flow system 600.

The IOP control system 200 shown in FIG. 2 may be used to address complications associated with under filtration of aqueous humor from the anterior chamber 70 (shown in FIGS. 1 and 5). For example, one complication associated with implantation of passive glaucoma drainage devices such as the primary drainage device 205 is the development of a fluid-filled bleb at the drainage site 212 shown in FIG. 5. The development of the bleb typically leads to scarring and fibrosis at the drainage site 212, which may lead to increased flow resistance through the primary drainage device 205. Generally, this resistance increases over time as the development and progression of fibrosis reduces or eliminates flow from the anterior chamber 70, eliminating the capacity of the primary drainage device 205 to affect IOP and resulting in a gradual increase in IOP. If a healthcare practitioner observes an unacceptable rise in IOP, the healthcare practitioner may decide to implant the secondary control device 215 to increase flow through the primary drainage device 205 by actively lowering the cracking pressure of the valve 610 and/or actively transitioning the flow system 600 into a more open condition.

In one embodiment, the secondary control device 215 is configured to affect IOP by adjusting the flow through the flow system 600 using the actuator 335. In particular, the flow system 600 within the primary drainage device 205 is configured to respond to the actuator 335 to affect the flow through the drainage tube 600. As described above, the valve 610 within the flow system 600 will assume an open condition when the fluid pressure proximal to the valve 610 surpasses a threshold cracking pressure of the valve 610. Thus, increasing the cracking pressure of the valve 610 increases the pressure threshold needed for the valve 610 to assume an open condition and allow fluid flow past the valve 610. Similarly, decreasing the cracking pressure of the valve 610 decreases the pressure threshold needed for the valve 610 to assume an open condition. In some embodiments, the actuator 635 acts on the flow system 600 to decrease the cracking pressure of the valve 610.

In an exemplary scenario, a healthcare provider can evaluate the current IOP and determine whether the aqueous humor is draining from the anterior chamber 70 in a desirable fashion. As time passes after the initial implantation of the primary drainage device 205, the initial cracking pressure threshold of the flow system 600 may not be ideal. After the initial drop in IOP after implantation, the IOP may gradually rise due to faulty drainage as a result of scarring at the drainage site (i.e., scarring or fibrosis of the bleb). The increase in drainage site pressure may hinder the passive flow of fluid through the primary drainage device 205 by decreasing the pressure differential across the primary drainage device 205, which causes a gradual increase in IOP. If the calculated IOP indicates that aqueous flow is occurring in an appropriate fashion, then no adjustment may be needed. If, however, the healthcare provider determines that the aqueous humor is not draining appropriately from the eye (e.g., if the IOP is not within a desired range, as determined by pressure measurements by the atmospheric pressure sensor 340 and the anterior chamber pressure sensor 345), the healthcare provider may then decrease the pressure threshold of the flow system 600 by implanting and using the secondary control device 215 to increase the aqueous flow from the anterior chamber 70 through the primary drainage device 205 to effect a pressure change to the desired IOP. To do this, the user can use the actuator 335 of the secondary control device 215 to adjust the flow system 600 by wirelessly adjusting the flow system 600, thereby changing the pressure drop across the primary drainage device 205. Thus, the secondary control device 215 may be implanted at the same time as the primary drainage device 205, or may be implanted at a later time during a subsequent revision or corrective procedure, as described above.

In some embodiments, the secondary control device 215 may be programmed (e.g., via the processor 320) to activate the actuator 335 when the IOP surpasses a predetermined threshold value. Likewise, in some embodiments, the secondary control device 215 may be programmed (e.g., via the processor 320) to deactivate the actuator 335 when the IOP falls below a predetermined threshold value. In some embodiments, these IOP threshold values or predetermined acceptable IOP range may be stored in the memory 325. In this fashion, the secondary control device 215 enables the user to change how the primary drainage device 205 responds to the pressure differential P1:P2 across the flow system 600 based on the changes in the IOP.

Figure 8:
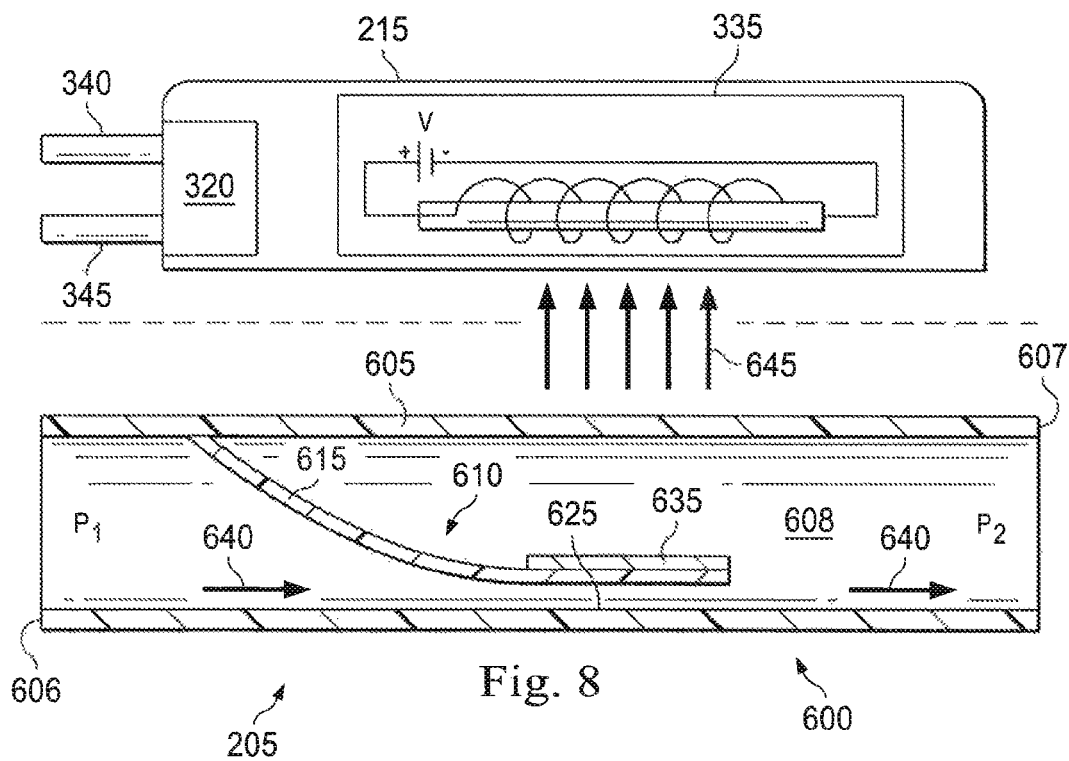
FIG. 8 is a stylized illustration of a cross-sectional view of the exemplary primary drainage device shown in FIG. 6 and an exemplary secondary control device according to the principles of the present disclosure and disposed within an eye.

FIG. 8 shows a stylized cross-sectional view of the secondary control device 215 and the primary drainage device 205. These may be implanted within the eye in different locations. For example, the secondary control device 215 may be implanted within the subconjunctival space, and the primary drainage device 205 may be implanted within the suprachoroidal space (as illustrated in FIG. 3). The flow system 600 in FIG. 8 is shown in an open condition, with aqueous fluid flowing through the valve 610 from the inlet 606 to the outlet 607 in the direction indicated by the arrows 640.

As shown in FIG. 8, upon activation of the actuator 335, the actuator 335 interacts with the valve 610 to lower the cracking pressure of the valve 610 and/or open the valve 610. The position of the sealing portion 615 is largely pressure-dependent until influenced by the secondary control device 215 to assume a more open position. In the pictured embodiment, the actuator 335 comprises an electromagnet configured to create an electromagnetic field (in response to an applied voltage) to influence the responsive element 635 on the sealing portion 615 of the valve 610. In the pictured embodiment, the responsive element 635 comprises a magnetic element that is responsive to the magnetic field created by the actuator 335. Upon activation of the actuator 335, the responsive element 635 is drawn through the fluid flow passageway 608 in the direction of the actuator 335, as indicated by the arrows 645. In other embodiments, the responsive element 635 and the actuator 335 may comprise other interactive elements capable of inducing movement of the responsive element 635 and the sealing portion 615. For example, in one embodiment, the responsive element 635 and the actuator 335 comprise radiofrequency (RF) coils that are configured to inductively power the mechanical shifting of the sealing portion 615 through the fluid flow passageway 608.

In the pictured embodiment, when the electromagnetic actuator 335 is activated and the responsive element 635 is drawn toward the actuator 335 in response to the magnetic force exerted on the responsive element 635 by the actuator 335, the sealing portion 615 is also drawn away from the valve seat 625 toward the actuator 615 because the responsive element 635 is coupled to the sealing portion 615. As the sealing portion 615 is drawn farther into the fluid flow passageway 608, the cracking pressure of valve 610 decreases and the fluid flow past the valve 610 progressively increases. Thus, in a scenario utilizing the secondary control device 215, the primary drainage device 205 may have a lower pressure threshold needed to be overcome to allow fluid to flow through the flow system 600 than in a scenario where the primary drainage device is passively operating to drain aqueous fluid in response to the pressure differential across the flow system 600.

The healthcare provider may repeatedly reevaluate the patient's IOP to assess whether aqueous humor is appropriately draining from the patient's eye. If not, the user may then readjust the pressure threshold of the flow device 300 by activating and/or deactivating the actuator 335 of the secondary control device 215 to affect the flow through the primary drainage device 205. For example, if the IOP achieves a desirable level, then the user may deactivate the actuator 335, thereby allowing the primary drainage device to return to a passive mode in which the valve 610 is largely pressure-dependent and the pressure differential across the sealing portion 615 dictates the flow through the flow system 600. Thus, by monitoring the IOP and actively throttling the valve 610 within the flow system 600, a desired IOP may be maintained.

Figure 9:
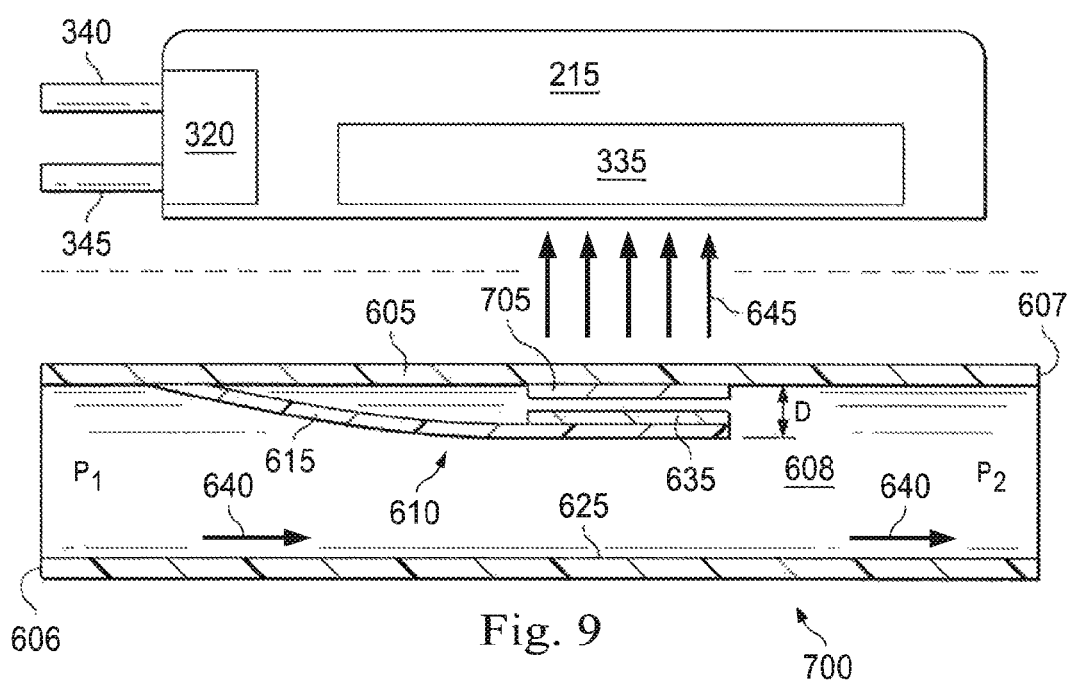
FIG. 9 is a stylized illustration of a cross-sectional view of an exemplary primary drainage device and an exemplary secondary control device according to the principles of the present disclosure and disposed within an eye.

FIG. 9 shows a stylized cross-sectional view of the secondary control device 215 and an exemplary primary drainage device 700 according to one embodiment of the present disclosure. The secondary control device 215 may be implanted within the subconjunctival space, and the primary drainage device 700 may be implanted within the suprachoroidal space (as illustrated in FIG. 3). The primary drainage device 700 is substantially similar to the primary drainage device 205 except for the differences shown or described. In particular, the primary drainage device 700 includes a latch element 705 configured to maintain the open condition of the valve 610 after actuation of the actuator 335 in the secondary control device 215. The primary drainage device 700 is shown in an open condition, with aqueous fluid flowing through the valve 610 from the inlet 606 to the outlet 607 in the direction indicated by the arrows 640. As described above, upon activation of the actuator 335, the responsive element 635 and the sealing portion 615 are drawn through the fluid flow passageway 608 toward the actuator 335. In the pictured embodiment, the latch element 705 comprises a magnetic element configured to attract and detachably couple to the responsive element 635 after the responsive element 635 reaches a predetermined distance D from the latch element 705. In different embodiments, the distance D may vary depending upon the particular structural and mechanical characteristics of the latch element 705. In other embodiments, the latch element 705 and the responsive element 635 may comprise any of a variety of mechanical coupling elements, such as, by way of non-limiting example, a bi-stable latch (magnetic or spring-based). Thus, the actuator 335 need not be continuously activated or powered to maintain the valve 610 in an open condition. Also, the latch element 905 may enable the secondary control device 215 to utilize less power to actuate the mechanical movement of the sealing portion 615 into a substantially open position. Upon deactivation of the actuator 335, the latch element 705 is configured to decouple from and release the responsive element 635.

Figure 10:
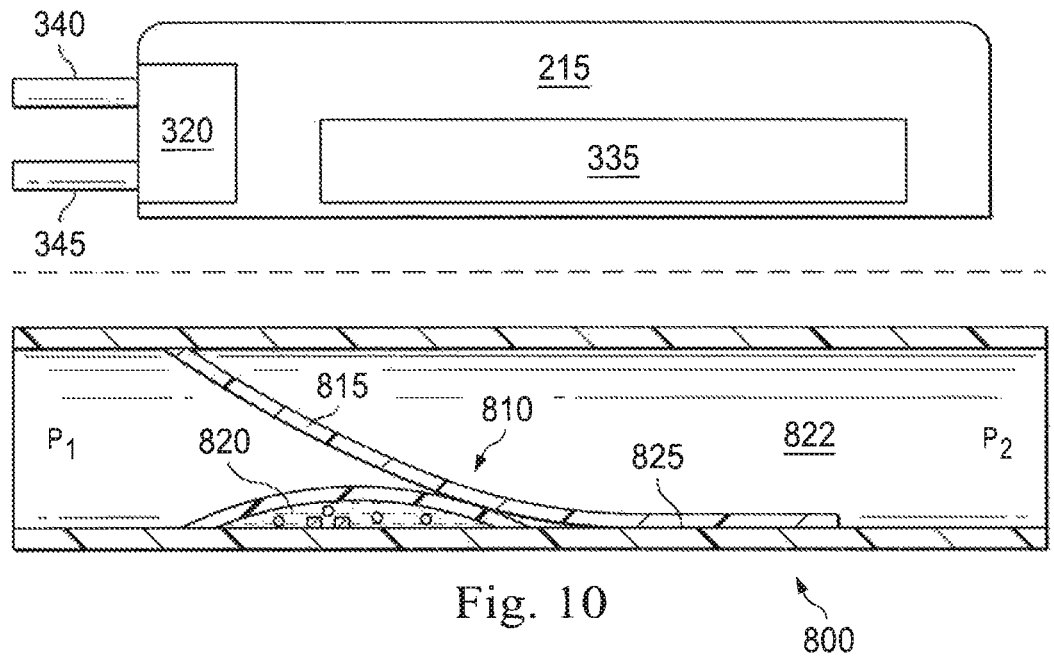
FIG. 10 is a stylized illustration of a cross-sectional view of an exemplary primary drainage device and an exemplary secondary control device according to the principles of the present disclosure.
Figure 11:
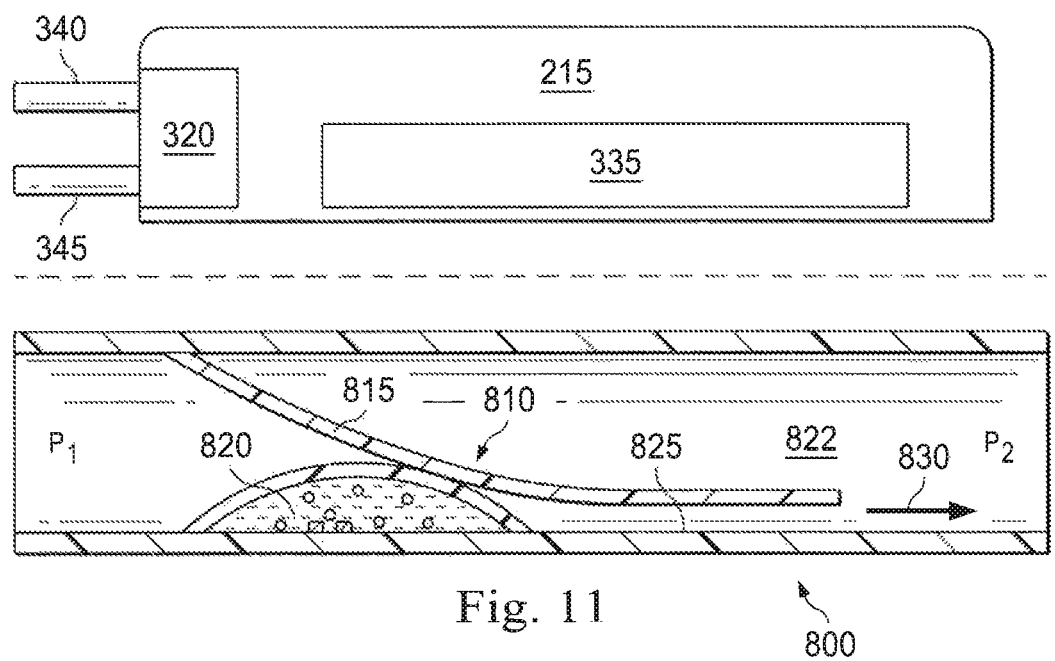
FIG. 11 is a stylized illustration of a cross-sectional view of the primary drainage device and the exemplary secondary control device shown in FIG. 10.

FIGS. 10 and 11 shows stylized cross-sectional views of the secondary control device 215 and an exemplary primary drainage device 800 according to one embodiment of the present disclosure. The secondary control device 215 may be implanted within the subconjunctival space, and the primary drainage device 800 may be implanted within the suprachoroidal space (as illustrated in FIG. 3). The primary drainage device 800 is substantially similar to the primary drainage device 205 except for the differences shown or described. In particular, the primary drainage device 800 includes a valve 810 that is substantially similar to the valve 610 except for the differences described herein. In particular, the valve 810 includes a sealing portion 815 and an adjustable boss element 820 disposed within a fluid flow passageway 822. In the pictured embodiment, the sealing portion 815 is substantially similar to the sealing portion 615 except that the sealing portion 815 lacks the responsive element 635. In FIG. 10, the primary drainage device 800 is shown in a closed condition where the sealing portion 815 rests upon a valve seat 825. The adjustable boss element 820 is configured to expand or rise into the fluid flow passageway 822 and push the sealing portion 815 away from the valve seat 825 into the fluid flow passageway 822 after actuation of the actuator 335 in the secondary control device 215.

In FIG. 11, the primary drainage device 800 is shown in an open condition, with aqueous fluid flowing through the valve 810 in the direction indicated by the arrow 830. As described above, upon activation of the actuator 335, the adjustable boss element 820 raises into the fluid flow passageway 822 and pushes the sealing portion 815 through the fluid flow passageway 608 toward the actuator 335. By moving the sealing portion 815 into the fluid flow passageway 822, the adjustable boss element 820 may decrease the cracking pressure of the valve 810 and thereby lower the pressure threshold needed to be overcome to allow fluid to flow past the valve 810. Upon deactivation of the actuator 335, the adjustable boss element 820 is configured to decrease in size or deflate, thereby returning the sealing portion 815 closer to a valve seat 825 and increasing the cracking pressure of the valve 810.

In the pictured embodiment in FIGS. 10 and 11, the adjustable boss element 820 comprises an electrolysis chamber with a flexible or deflectable membrane surface that expands to push the sealing portion 815 further into the fluid flow passageway 822. An example of an electrolysis chamber is described in U.S. Patent Publication 2013/0144202 to Field et al., which is incorporated herein by reference in its entirety. In some embodiments, the adjustable boss element 810 does not block the flow channel or fluid flow passageway 822 as it expands because aqueous fluid may flow around and over the adjustable boss element 810 (e.g., in the into and out-of-plane directions). In other embodiments, the adjustable boss element 820 may comprise any of a variety of movable or expandable elements, such as, by way of non-limiting example, piezoelectric actuators, linear displacement actuators (rack and gear), and electromagnetic actuators.

Figure 12:
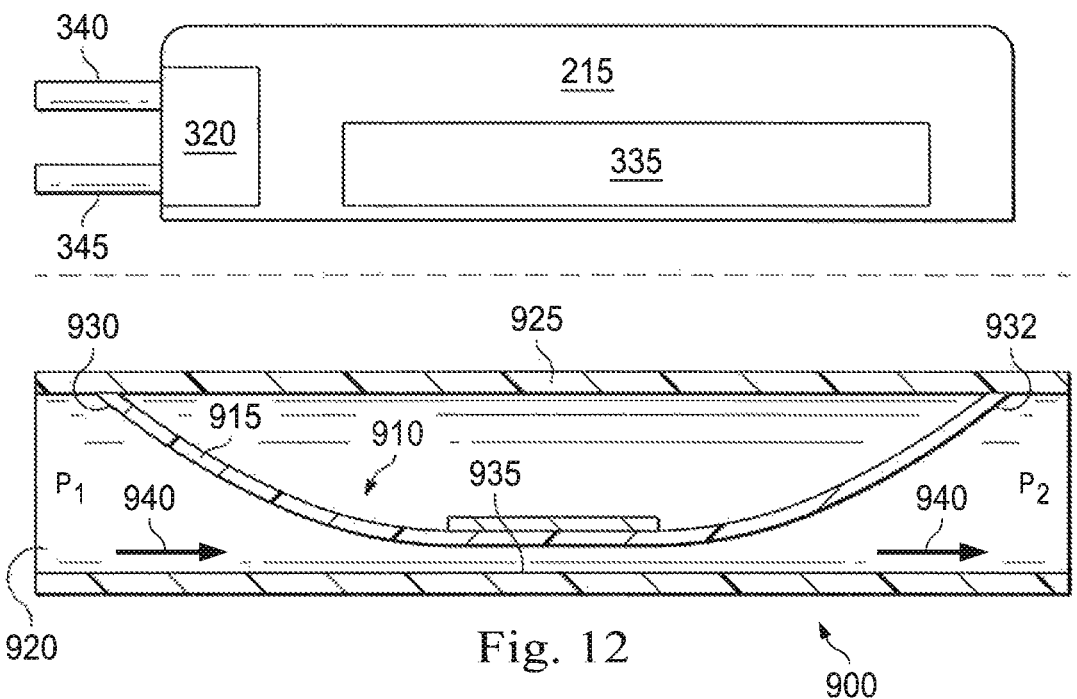
FIG. 12 is a stylized illustration of a cross-sectional view of an exemplary primary drainage device and an exemplary secondary control device according to the principles of the present disclosure.

FIG. 12 shows a stylized cross-sectional view of the secondary control device 215 and an exemplary primary drainage device 900 according to one embodiment of the present disclosure. The secondary control device 215 may be implanted within the subconjunctival space, and the primary drainage device 900 is shown implanted within the suprachoroidal space (as illustrated in FIG. 3). The primary drainage device 900 is substantially similar to the primary drainage device 205 except for the differences described or shown. In particular, the primary drainage device 800 includes a valve 910 that is substantially similar to the valve 610 except for the differences described or shown. In particular, the valve 910 includes a sealing portion 915 disposed within a fluid flow passageway 920 defined by a housing 925. In the pictured embodiment, the sealing portion 915 is substantially similar to the sealing portion 915 except that the sealing portion 915 lacks the responsive element 635 and the sealing portion 915 is attached to the housing 925 at two separate attachment points 930, 932.

In FIG. 12, the primary drainage device 900 is shown in an open condition where the sealing portion 915 is raised away from a valve seat 935 to allow fluid to flow through the drainage device 900 in the direction of the arrows 940. In the pictured embodiment, the actuator 335 of the secondary control device 215 is configured to change the physical characteristics of the sealing membrane 915 upon activation of the actuator 335. In one embodiment, activation of the actuator 335 adjusts (e.g., by way of non-limiting example, expands, contracts, rotates, or moves) the attachment points 930, 932 to change the "stiffness" of the sealing portion 915. Changing the stiffness of the sealing portion may affect the cracking pressure of the valve 910, as described above. If the change in stiffness decreases the cracking pressure of the valve 910, the actuator 335 can thereby lower the pressure threshold needed to be overcome to allow fluid to flow past the valve 910. Upon deactivation of the actuator 335, the attachment points 930, 932 are configured to resume their native positions, thereby returning the sealing portion 915 to its native position and the cracking pressure of the valve 910 to its original value.

In another embodiment, the sealing portion 915 may be formed from an active material such as, by way of non-limiting example, an electroactive polymer (EAP) that changes shape when stimulated by an electric field. In this embodiment, upon activation of the actuator 335, the actuator 335 may generate an electric field designed to change the physical characteristics of the sealing portion 915 in order to achieve the desired cracking pressure of the valve 910. By decreasing the cracking pressure of the valve 910, the actuator 335 may thereby lower the pressure threshold needed to be overcome to allow fluid to flow past the valve 910. Upon deactivation of the actuator 335, the sealing portion 915 is configured to resume its native physical characteristics, thereby returning the cracking pressure of the valve 910 to its original value.

Figure 13:
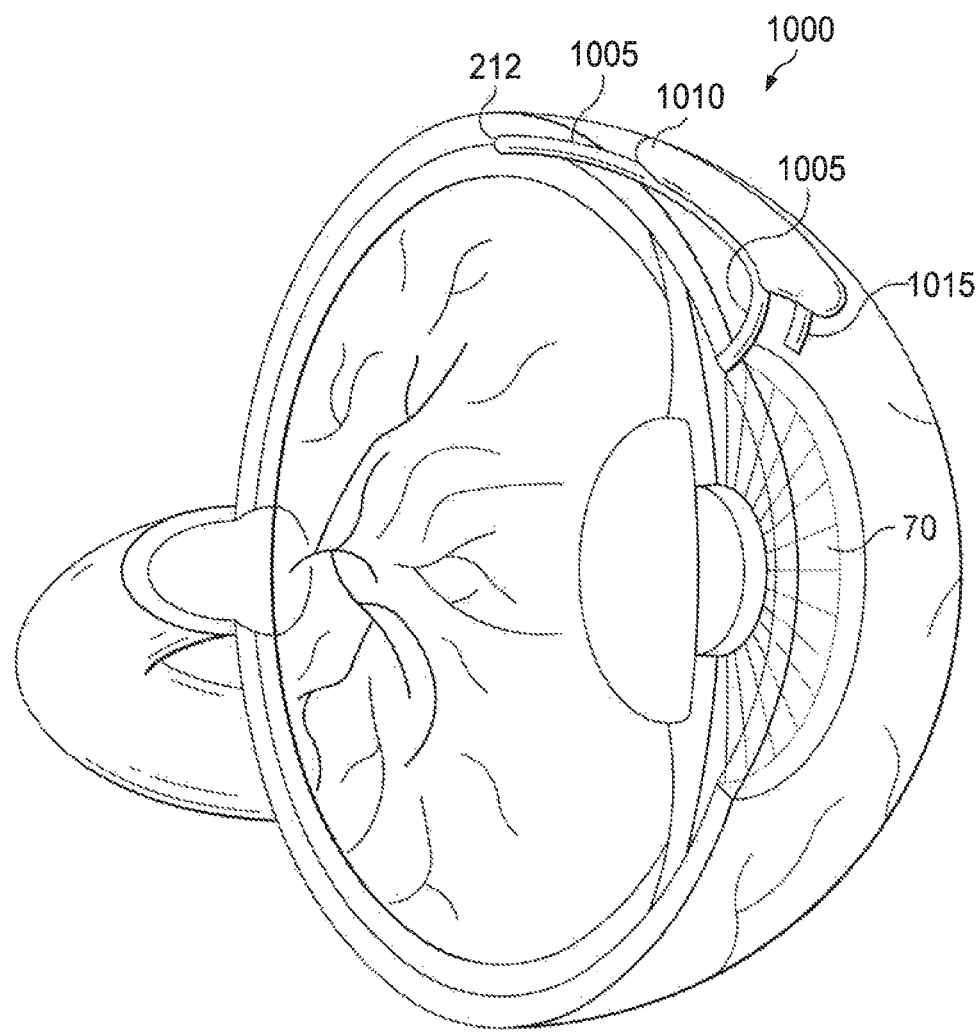
FIG. 13 is an illustration of an exemplary flow-regulating system disposed in the eye in accordance with one embodiment of the present disclosure.

FIG. 13 shows an IOP control system 1000 disposed on an eye to treat an ocular condition according to one exemplary aspect of the present disclosure. The IOP control system 1000 comprises a single, unitary implant carrying both a drainage device 1005 and a control device 1010. The drainage device 1005 may be substantially similar to the primary drainage device 205 described above, and the control device 1010 may be substantially similar to the secondary control device 205 described above.

In the pictured embodiment, the IOP control system 1000 is implanted within the eye to extend from the anterior chamber 70 to the drainage site 212. In the pictured embodiment, the drainage site 212 is the suprachoroidal space. In other embodiments, the drainage site 212 may be located elsewhere. The IOP control system 1000 may include, by way of non-limiting example, any number of drainage tubes, valves, pumps, transducers, processors, actuators, or sensors. In the pictured embodiment, the IOP control system 1000 is configured to fit at least partially within the subconjunctival space or the suprachoroidal space and is sized for example within a range between about 150 mm$^2$ to about 400 mm$^2$ In some embodiments, the IOP control system 1000 has a thickness less than about 2.5 mm thick. For example, in one embodiment, the IOP control system 1000 has a thickness of about 2.0 mm thick. The IOP control system 1000 may be curved to approximate the radius of the eye globe. In some embodiments, the IOP control system 1000 is rigid and preformed with a curvature suitable to substantially conform to the globe. In other embodiments, the IOP control system 1000 is flexible to conform to the globe. The above dimensions and arrangement are exemplary only, and other sizes and arrangements are contemplated.

In the pictured embodiment, the drainage device 1005 is shaped and sized to extend from the anterior chamber 70 of the eye to the drainage site 212 in the suprachoroidal space. The drainage device 1005 bridges the anterior chamber 70 and the drainage site 210 to provide an auxiliary flow path for aqueous humor, bypassing the flow-resistive conventional pathway through the trabecular meshwork and shunting aqueous humor directly to the drainage site 212. In the example shown, the drainage device 1005 is a single hollow tube having a single lumen. Other embodiments include a plurality of tubes or a plurality of lumens cooperating together to permit fluid to flow through the implantable system 1000. Aqueous humor may drain through the drainage device 1005 from the anterior chamber 70 to the drainage site 212 to alleviate elevated intraocular pressure conditions.

In the pictured embodiment, the implantable IOP control system 1000 includes the control device 1010. As described above with reference to the secondary control device 215 shown in FIG. 4, the control device 1010 is arranged to carry various components of an IOP control system, and may include transducers or sensors, a processing system, a memory, drug delivery components, a power source, an actuator, and/or other components that may be used to either control the IOP control system 1000 or otherwise treat ocular conditions. For example, in the pictured embodiment, an atmospheric pressure reference element 1015 extends from the control device 1010. In some embodiments, the atmospheric pressure reference element 1015 comprises a pressure sensor.

The control device 1010 may be curved to approximate the radius of the eye globe. In some embodiments, the control device 1010 is rigid and preformed with a curvature suitable to substantially conform to the globe. In other embodiments, the control device 1010 is flexible to conform to the globe. When implanted, the IOP control system 1000 may be located in the subconjunctival pocket between the conjunctiva and sclera. It may be generally located on an ocular quadrant commonly used for conventional glaucoma drainage devices with plates; that is, it may be located between neighboring ocular muscles that define the ocular quadrant chosen for implantation. In the pictured embodiment, the control device 1010 is shaped as a plate and is configured to fit at least partially within the subconjunctival space and is sized for example within a range between about 15 mm×10 mm to about 30 mm×15 mm. In some embodiments, the control device 1010 has a thickness less than about 2 mm thick. For example, in one embodiment, the control device 1010 has a thickness of about 1 mm thick. The above dimensions and arrangement are exemplary only, and other sizes and arrangements are contemplated.

Figure 14:
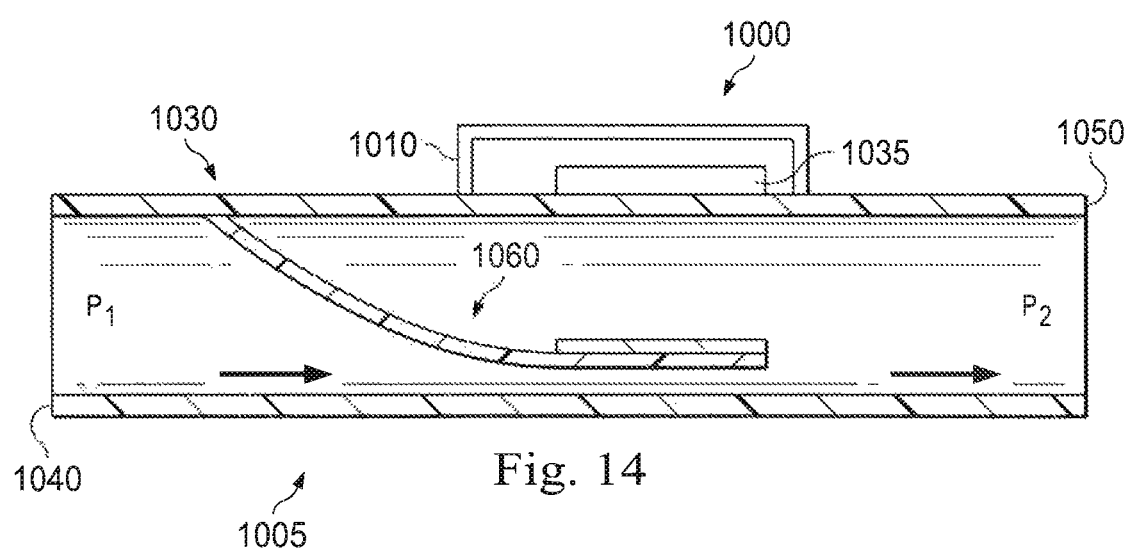
FIG. 14 is a stylized illustration of a cross-sectional view of the flow-regulating system shown in FIG. 13.

FIG. 14 shows a stylized cross-sectional view of the implantable IOP control system 1000 shown in FIG. 13. The drainage device 1005 includes a flow system 1030 that may be the same as the flow system 210 discussed with reference to FIGS. 2 and 5. The IOP control system 1000 comprises a single implant carrying both the drainage device 1005 and the control device 1010, which monitors the IOP. The IOP control system 1000 is designed to allow passive drainage of aqueous humor through the drainage device 1005 if the pressure differential between the pressure zone P1 at an inlet 1040 and the pressure zone P2 at an outlet 1050 (corresponding to the pressure zones P1 and P2 shown in FIG. 5) exceeds the threshold cracking pressure of a valve 1060 within the drainage device 1005. In the pictured embodiment, when an actuator 1035 of the control device 1010 is inactive, the fluid flow through the drainage device 1005 is dependent upon the pressure differential between the pressure zones P1:P2.

If and when a healthcare provider deems it necessary to begin active control of the drainage device (e.g., when passive drainage through the device 1005 is not sufficiently controlling the anterior chamber pressure and/or the IOP), the healthcare provider may activate the control device 1010. The control device may monitor the IOP and decide whether or not to activate the actuator and actively throttle flow through the drainage device 1005 based on the changes in IOP over time. Upon activation of the actuator 1035 in the control device 1010, the actuator 1035 affects the drainage device 1005 to actively throttle flow through the drainage device 1005 based on the IOP. The actuator 1035 may actively throttle flow through the drainage device 1005 through any of the methods described above with relation to FIGS. 6-12.

While generally described with the valves in the drainage devices having an open and closed condition, it is understood that the valve conditions may be opened by varying degrees and the system may operate to control each valve by opening and closing one or more valves to a greater or lesser amount as described to control the flow through the drainage devices.

The devices, systems, and methods described herein achieve IOP control with a relatively small device that allows for both passive and active IOP control. Due to the design of the IOP control systems disclosed herein, the overall size of at least the initial implant may be minimized, allowing for implantation in confined areas such as the suprachoroidal space. The embodiments utilizing separate primary drainage devices and secondary control devices decrease the invasiveness of the individual surgical procedures required to implant the separate devices, which may improve surgical outcomes. In some exemplary aspects, the initial implant may comprise a drainage device configured to allow passive aqueous outflow, which minimizes the size and invasiveness of the implant. Whether to improve the effectiveness of the drainage device or to provide necessary control arising from a change in the patient's medical needs, a healthcare provider may decide to implant the secondary control device to enable active control of aqueous outflow through the drainage device. This staged approach allows the doctor to have an added degree of discretion when balancing surgical risk with the needs of their patient.

The embodiments utilizing a single implant carrying both the primary drainage device and the secondary control device allow the doctor to employ a similarly staged approach by initially allowing passive drainage through the primary drainage device and only later implementing active control if necessary. Upon implantation, the combination device would utilize passive drainage control, thereby preserving power for IOP monitoring and subsequent active control, if necessary. Also, if the control device were to fail, the implant would be able to revert to the passive state through the drainage tube and maintain at least some degree of passive outflow through the drainage device.

The exemplary system disclosed herein allows the user to take into account intraocular pressures, bleb pressures, and/or the post-operative time lapse in regulating drainage flow. The IOP control system disclosed herein may work to extend the longevity of the drainage device by allowing a user to actively control the pressure differential threshold of the drainage devices, thereby enabling the device to remain effective at controlling IOP for a longer period of time as the pressure increases at the drainage site (e.g., secondary to bleb scarring or fibrosis). In addition, the exemplary IOP control system disclosed herein may not require a continuous power supply to maintain such adjustments.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An IOP control system for implantation in an eye of a patient, comprising:
   a drainage device sized for implantation into the eye of the patient and comprising:
      a housing including an inlet port and an outlet port;
      a fluid flow passageway extending through the housing from the inlet port to the outlet port to allow the flow of fluid from the inlet port to the outlet port; and
      at least one valve disposed within the drainage device, the at least one valve including a first side, an opposing second side, the at least one valve configured to affect flow through the fluid flow passageway from the inlet port to the outlet port by moving in response to pressure differentials acting on the opposing first and second sides; and
   a control device comprising an actuator including an activated mode and a deactivated mode, wherein the actuator in the activated mode is configured to selectively adjust flow through the drainage device in response to changes in intraocular pressure wherein the at least one valve comprises a sealing portion attached to the housing and being shaped and configured to control flow of aqueous humor through the fluid flow passageway by deflecting in response to pressure differentials acting across the sealing portion, and wherein the at least one valve is in a closed condition when the sealing portion contacts a valve seat in the housing; wherein the sealing portion is movable relative to the valve seat in response to pressure differentials acting on the opposing first and second sides, is movable relative to the housing in response to activation of the actuator, and includes a responsive element that is configured to interact with the actuator and move the sealing portion relative to the valve seat when the actuator is in an activated mode; wherein the responsive element comprises a magnetic element and the actuator comprises an electromagnet configured to attract the magnetic element when the actuator is in an activated mode.

2. The IOP control system of claim 1, wherein the sealing portion is configured to move through the fluid flow passageway in the direction of the actuator when the actuator is in an activated mode.

3. The IOP control system of claim 1, wherein the sealing portion is configured to change in stiffness when the actuator is in an activated mode.

4. The IOP control system of claim 1, further including a processor in the control device, the processor being configured to selectively implement at least one of a plurality of different control algorithms for IOP control.

5. The IOP control system of claim 4, wherein the processor may be re-programmed to selectively implement at least one of a plurality of different control algorithms for IOP control.

6. The IOP control device of claim 5, further including an external controller, the external controller configured to re-program the processor.

* * * * *